United States Patent [19]

Scott

[11] Patent Number: 4,578,989
[45] Date of Patent: Apr. 1, 1986

[54] CONCRETE SLUMP MEASURING DEVICE

[76] Inventor: James D. Scott, 13845 Soldberg Rd. SE., Yelm, Wash. 98597

[21] Appl. No.: 753,766

[22] Filed: Jul. 10, 1985

[51] Int. Cl.$^4$ ............................................. G01N 11/00
[52] U.S. Cl. ........................................ 73/54; 33/379; 33/451
[58] Field of Search ..................... 73/54, 291; 33/451, 33/379, 343, 126.7 R

[56] References Cited

U.S. PATENT DOCUMENTS

| | | |
|---|---|---|
| 3,009,250 | 11/1961 | Schock . |
| 3,403,546 | 10/1968 | Stratton ................................. 73/54 |
| 3,631,712 | 1/1972 | Mercier ................................. 73/54 |
| 3,640,121 | 2/1972 | Mercier ................................. 73/54 |
| 3,863,494 | 2/1975 | Nasser ................................... 73/54 |
| 3,924,447 | 12/1975 | Garrison ............................... 73/54 |
| 4,356,723 | 11/1982 | Sims ..................................... 73/54 |
| 4,404,753 | 9/1983 | Klok ..................................... 33/451 |

Primary Examiner—Stewart J. Levy
Assistant Examiner—Joseph W. Roskos
Attorney, Agent, or Firm—Seed and Berry

[57] ABSTRACT

A slump indicator instrument for measuring the slump of a concrete mix while in the discharge chute of a concrete mixing truck. The indicator has angled sides for setting the discharge chute at a predetermined angle. The instrument has calibration markings for determining the slump of a concrete mix when the indicator is inserted into a mix in a discharge chute set at the predetermined angle.

16 Claims, 3 Drawing Figures

CONCRETE SLUMP MEASURING DEVICE

TECHNICAL FIELD

The invention generally relates to a method and apparatus for measuring concrete slump. Specifically, the invention relates to a method and apparatus for measuring the slump of a specific concrete mix while in the discharge chute of a concrete mixing truck.

BACKGROUND OF THE ART

A variety of tests are presently available to measure the quality of unset concrete which is indicative of the strength and quality the concrete will have after it has set. The quantity of water contained in a concrete mix bears directly on the quality and strength of the finished concrete. A standard measure of the quantity of water in a concrete mix can be determined by measuring the slump of the mix. Slump is a measure of the degree to which a volume of unset concrete will settle when allowed to stand.

Typically, enough concrete is gathered from the discharge chute of a concrete mixing truck to fill a testing cone. The testing cone is a hollow frustum of rigid material having an opening at the top and an opening at the bottom. The cone is usually twelve inches high. The open bottom typically has a ten inch diameter and the open top typically has a four inch diameter. Concrete is packed into the cone in three equal layers and is tamped twenty-five strokes per layer. The cone is then topped off with concrete so that the concrete is flush across the top opening. The cone is then twisted gently and raised carefully off the concrete which then sags or slumps. The empty cone is placed next to the concrete so that the difference between the height of the cone and the height of the concrete can be measured. This difference in inches is the slump of the concrete.

This test is both time-consuming and subject to inaccuracies due to human variation. If the cone is not loaded properly or tamped properly an incorrect measurement will result. It often takes five or six minutes to complete the test. If the slump is greater than the known allowable slump for the specific mix in question, then the concrete mix contains too much water and must either be rejected or adjusted. Often, concrete is being discharged while an examiner completes the slump test. If the concrete fails the slump test, the remainder of the load must be rejected.

DISCLOSURE OF THE INVENTION

It is an object of the invention to quickly and accurately determine the slump of a specific concrete mix while in the discharge chute of a conventional cement mixing truck before the mix is poured.

Basically, the invention achieves this objective by providing a concrete slump measuring device which can repeatedly set the discharge chute at a predetermined slope angle with repect to the horizon and which has been calibrated to measure the slump of a specific concrete mix while in the discharge chute at the predetermined angle.

In one embodiment, the slump measuring device, or slump indicator, has a substantially triangular body. The body has a base, a first side and a second side. The first and second sides form acute angles with the base. A mechanism for repeatedly, horizontally aligning the slump indicator is provided. When so aligned, the first and second sides form predetermined angles with respect to the horizon for setting the angle of the discharge chute. For example, the first side can form an eighty degree angle with the base, and the second side a seventy-five degree angle with the base. Thus, when the indicator is aligned with the horizon the first side will drop away from the horizontal at a ten degree angle and the second side will drop away at a fifteen degree angle. The indicator is then used as a leveling device to set the slope angle of the discharge chute to one of two predetermined slope angles.

Two discharge angles are provided so that the chute can be set at lesser or greater angles dpending on the heights of the discharge chute. A greater angle is preferred for use with average truck chutes and a lesser angle is preferred for use with trucks having lower chutes or with concrete pumps having a high hopper. Other predetermined angles for the sides can be used as desired.

Once the discharge chute has been adjusted to one of the slope angles corresponding to the horizontal angular displacement of the first or second side, concrete is allowed to flow down the discharge chute. The concrete is discharged until a small amount of concrete has fallen off the end of the chute. The flow of concrete is then stopped. The base of the slump indicator is inserted into the static concrete mass and into contact with the lowest point in the chute at a place in the concrete near the end of the chute wherein the concrete has essentially uniform depth. The sides of the indicator are calibrated with markings which indicate the slump of the concrete mix. The level of the concrete on the slump indicator is then read off the appropriately calibrated side corresponding to the angle at which the discharge chute was set. Thus, a quick and accurate determination of slump can be made before the concrete is poured.

The calibrations on the first and second sides of the slump indicator body are determined empirically for any specific concrete mix. For example, a sample of a known concrete mix is subjected to the standard concrete slump test utilizing the testing cone and tamping procedure. After determining the slump of the concrete in this conventional manner, an uncalibrated slump indicator in accordance with the present invention, is inserted into the discharge chute of the cement mixer from which the sample was taken, with the chute set at a slope angle corresponding to the angle of the first body sides to be calibrated. The level of the concrete on the slump indicator is then noted and engraved or otherwise marked on the side of the body. This procedure is then repeated for the same concrete mixture having various slumps. The procedure is also repeated for the second side of the body using a chute slope angle corresponding to the angle of the second side. The slump indicator thus calibrated, can be used in the field to measure the slump of a known concrete mix in the discharge chute of the concrete truck.

BEST MODE FOR CARRYING OUT THE INVENTION

Figure 1:
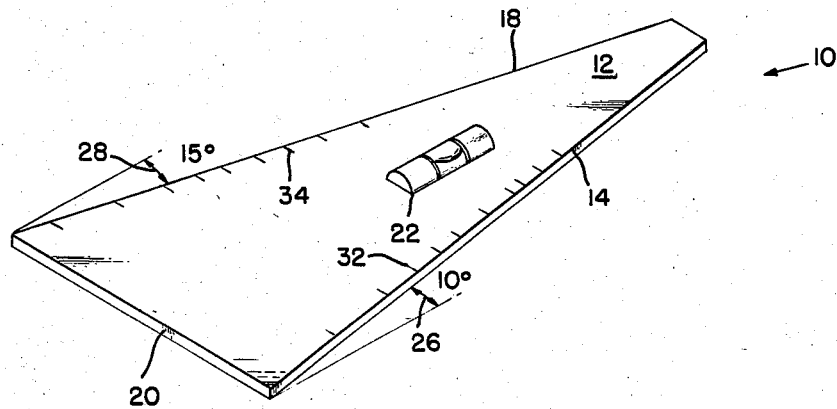
FIG. 1 is an isometric view of a slump indicator in accordance with the present invention.

Referring now in detail to the drawing, the numerals herein referred to like numbered parts in the figures.

In FIG. 1, a slump indicator, in accordance with the present invention, is generally indicated by reference numeral 10. The indicator has a plate body 12, with a first side 14, a second side 18 and a base 20 forming a substantially triangular shape with a truncated apex. The body can be constructed from any material which will provide sufficient rigidity and durability including metal, plastic or any other suitable material.

Figure 2:
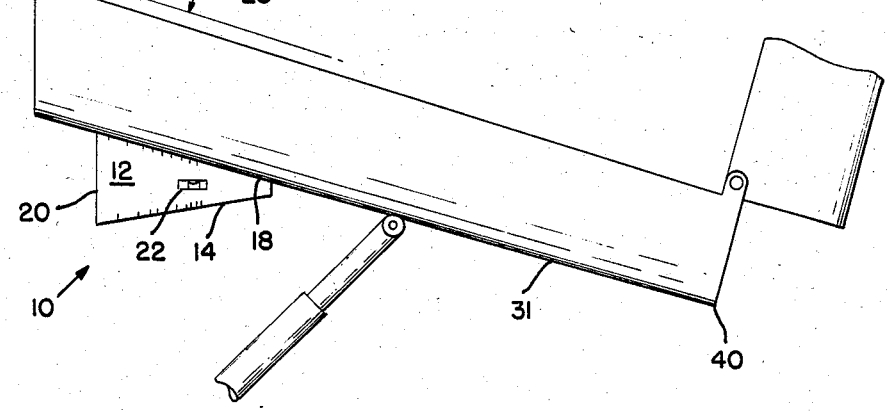
FIG. 2 is a side elevational view of the slump indicator and a conventional discharge chute illustrating the use of the slump indicator to set the angle of the discharge chute.

A bubble level 22, or other horizon finding mechanism, is provided on the body 12 to establish a horizontal reference for the sides 14, 18. The first side 14 and second side 18 form a first predetermined angle 26 and a second predetermined angle 28, respectively, with the horizon, when the indicator 10 is held in a vertical plane and horizontally aligned, as shown in FIG. 2, by the use of the bubble level. It has been found that first and second predetemined angles of ten degrees and fifteen degrees, respectively, provide chute discharge slope angles which are typically used with conventional cement mixing trucks for different applications. For example, the fifteen degree discharge slope angle is used for typical pouring situations. The ten degree angle can be used to discharge concrete mix into an elevated concrete pump hopper.

The bubble level 22 is positioned along the longitudinal center line of the body so that the first and second sides form the predetermined angles 26, 28 when the body is aligned with the horizon. The body may form any shape desired so long as a portion thereof indicates a discharge chute slope setting angle when the body is oriented with respect to the horizon using a horizon finding mechanism.

The slump indicator 10, constructed in this manner, provides a device which can be used to uniformly set the slope angle of the discharge chute 31 of a concrete truck according to the predetermined first or second angles. Thus, if the slump indicator is leveled using the bubble level 22 and the discharge chute is aligned with the first side 14, the discharge chute will form a 10 degree angle with the horizon to provide a relatively slow flow of concrete from the discharge chute. If the slump indicator is leveled and the discharge chute is aligned with the second side 18 of the body 12, as shown in FIG. 2, the discharge chute will be declined 15 degrees from the horizon.

Calibrations 32 and 34 are provided on the first side 14 and second side 18, respectively, of the body 12. The calibrations correspond to slump measurements for a concrete mix of the type with which the slump indicator 10 is to be used. These calibrations are empirically determined and correspond to a range of typically encountered slumps for a particular known concrete mix.

To calibrate the sides 14 and 18 of the slump indicator 10, a known mixture of concrete is prepared. A conventional slump test is then run on this mixture and the slump is determined in inches. This mixture is then discharged through the discharge chute 31 of a cement mixing truck. The discharge chute is first set at a horizontal slope angle corresponding to one of the predetermined angles 26 or 28 on the slump indicator for the side 14 or 18 which is to be calibrated. When concrete mixture begins to fall off a lower end 40 of the discharge chute 31, the flow is stopped.

Figure 3:
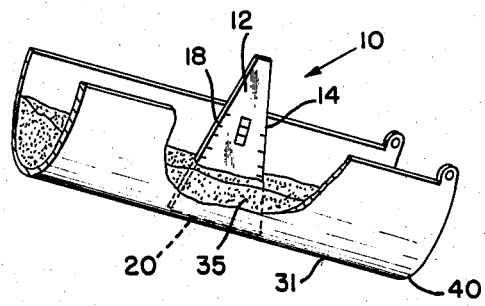
FIG. 3 is a perspective view of the slump indicator in use with a mass of concrete mix in the discharge chute.

As seen in FIG. 3, the base 20 of the slump indicator is inserted into the mass 35 of concrete mixture in the discharge chute 31 at a measuring location where the depth of the concrete mass is relatively uniform toward the end 40 of the chute. The body 12 is pushed downward into the concrete mass 35 until the full length of the base 20 engages the lowest part of the bottom of the chute to provide a repeatable positioning of the indicator. The body is inserted so as to be generally parallel with the flow of concrete in the chute, rather than crosswise to the flow.

The level of the concrete mass 35 is then engraved or otherwise marked on the side of the slump indicator being calibrated. This level corresponds to the slump measurement in inches determined by the conventional test. This procedure is then repeated for the same mixture but with different slumps. In this manner, the side of the indicator being calibrated may be calibrated for a range of slumps for a given type of concrete mixture. The procedure is then repeated for the other side of the indicator.

When using the slump indicator 10 in the field, the slump measurment is made in much the same manner as described for calibrating the indicator. The slope angle of the discharge chute 31 is first set at a discharge angle according to either the first side 14 or second side 18 of the indicator. In FIG. 2, the discharge chute has been set to an angle of fifteen degrees by aligning the chute with the second side 18 of the indicator 10 after aligning the body 12 horizontally using the bubble level 22. The mixture 35 is discharged until the mixture begins to fall off the end of the chute. As shown in FIG. 3, the base 20 of the indicator 15 is inserted into the lowermost portion of the curved chute at the measuring location near the end of the chute where the concrete depth is relatively uniform and parallel with the flow. The slump measurement for the mixture is indicated by the level of the concrete mass corresponding to the nearest calibration mark on the second side 18. Subsequent measurements can be quickly made of the mixture to confirm the slump measurement by momentarily stopping the discharge flow and inserting the indicator at the measuring location. Thus, measurements of slump can be made quickly and frequently during the pouring procedure, and the slump of the mixture adjusted if necessary. In this manner, the pouring of a mixture with improper slump can be avoided with a minimum of inconvenience.

In addition to the first predetermined angle 26 of 10 degrees and the second predetermined angle 28 of 15 degrees, other chute slope angles may be used, provided the corresponding first side 14 and second side 18 are correctly calibrated for those slope angles. Varying these angles will provide for different flow rates during discharge. For extremely viscous mixtures a large horizontal chute angle may be desired to provide accurate readings. For less viscous mixtures a smaller chute angle may be employed while maintaining the accuracy of the measurement.

Other embodiments and variations of the invention are also contemplated. These embodiments and variations employ the same charecteristics and essential features of the invention as described. For example, the shape of the body 12 need not be triangular. Any shape which allows the body to be used to repeatedly reference the discharge chute to the horizon to set slope angle is suitable. Thus, the scope of the invention is not to be limited by the above description but is to be determined by the scope of the claims which follow.

I claim:

1. A slump indicator for a knwon concrete mix to measure the water content of the mix while in a discharge chute prior to discharge from the chute, comprising:
   means for establishing a reference relative to the horizon;
   means for setting the discharge chute relative to the reference at a predetermined angle from the horizon;
   means for repeatably orienting the slump indicator in a measuring position within the discharge chute; and
   means for visually indicating a conrete mix height corresponding to the slump measurement of the concrete mix when the slump indicator is in the measuring position in the discharge chute after the discharge chute is set at the predetermined angle and contains a static load of the known concrete mix.

2. The slump indicator of claim 1 wherein the means for setting the discharge chute at the predetermined angle includes a body having a side angularly disposed relative to the horizon at the predetermined angle whereby the discharge chute can be aligned with the side to set the discharge chute at the predetermined angle.

3. The slump indicator of claim 2, wherein the body includes a second side angularly disposed relative to the horizon at a second predetermined angle larger than the first predetermined angle, whereby the discharge chute can be aligned with the second side to set the discharge chute at the second predetermined angle.

4. The slump indicator of claim 3 wherein the first predetermined angle is substantially 10 degrees and wherein the second predetermined angle is substantially 15 degrees.

5. The slump indicator of claim 2 wherein the means for establishing the reference is a bubble level.

6. The slump indicator of claim 2 wherein the means for repeatably orienting the slump indicator in the measuring position within the discharge chute is a chute engaging side of the body, the chute engaging side being shaped to engage the lower most portion of the inside wall of the chute and hold the body stable against movement while in the measuring position.

7. The slump indicator of claim 2 wherein the means for visually indicating the concrete mix height is a series of calibrated height markings on the body side corresponding to measured slumps for the known concrete mix with which the indicator is to be used.

8. A slump indicator for a known concrete mix to measure the water content of the mix while in a discharge chute prior to discharge from the chute, comprising a body having a chute engaging portion and at least one chute alignment portion, the body further having calibrations corresponding to various slumps for the concrete mix and means for establishing a horizotal reference, the chute alignment portion being angularly oriented from the horizontal reference for adjusting the discharge chute to a predetermined angle relative to the horizontal reference, the chute engaging portion being insertable into the concrete mix in the discharge chute for engagement with the chute bottom, the calibrations being marked to indicate concrete mix heights corresponding to various slumps of the concrete mix.

9. The slump indicator of claim 8 wherein the chute alignment portion is a side of the body.

10. The slump indicator of claim 9, further including a second chute alignment portion comprising a second side of the body angularly oriented from the horizontal reference for adjusting the discharge chute to a second predetermined angle relative to the horizontal reference.

11. The slump indicator of claim 10 wherein the body is generally triangular in shape, with the first and second chute alignment sides forming two sides of the triangle, and the chute engaging portion is a third side of the body forming the base of the triangle, the calibrations indicating concrete mix heights relative to the third side.

12. A slump indicator for a known concrete mix to measure the water content of the mix while in a discharge chute prior to discharge from the chute comprising a plate body manually insertable into the concrete mix in the discharge chute and having an edge side for engaging the lowermost portion of the inside wall of the chute, with the body substantially parallel to the flow direction of the chute, the edge side being shaped for holding the body stable against movement during slump measurement, the body further including calibration markings indicating concrete mix heights relative to the edge side of the body in the chute corresponding to various slumps of the concrete mix.

13. The slump indicator of claim 12 further including means for establishing a reference relative to the horizon, and wherein the body includes a second edge side angularly oriented from the reference for alignment of the discharge chute therewith to set the discharge chute at a predetermined angle relative to the horizon.

14. A method for measuring the slump of a specific concrete mix while in a discharge chute, comprising the following steps:
   angularly orienting the discharge chute to a predetermined angle relative to the horizon;
   causing concrete mix to flow down the chute;
   stopping the flow of the concrete mix in the chute after a portion of the concrete mix has begun to fall off the discharge end of the chute;
   measuring the depth of the concrete mix in the chute at a measuring location toward the end of the chute; and
   comparing the measured depth to prior depth measurements for the same specific concrete mix having various known slumps, taken in similarly oriented chutes, the prior depth measurement closest to the measured depth indicating the approximate slump of the concrete mix being measured.

15. The method of claim 14 wherein the step of measuring the depth of the concrete mix in the chute and the step of comparing the measurement to prior depth measurements are accomplished by using a slump indicating instrument having means for repeatedly orienting the instrument in a measuring position at the measuring location, the instrument having calibration markings corresponding to depth measurements for various known slumps for the specific concrete mix taken in a chute oriented at the same predetermined angle, and by visually reading the calibration marking corresponding to the level of the top of the concrete mix in the chute to determine the approximate slump of the concrete mix being measured in the chute.

16. The method of claim 15 wherein the step of angularly orienting the discharge chute is accomplished by establishing a reference relative to the horizon wherein the instrument has means for setting the discharge chute at the predetermined angle relative to the horizontal reference and by aligning the chute with the chute angle setting means.

* * * * *